United States Patent
Zhao et al.

(10) Patent No.: US 7,706,124 B2
(45) Date of Patent: Apr. 27, 2010

(54) FILTERING CAPACITOR FEEDTHROUGH ASSEMBLY

(75) Inventors: Jennifer J. Zhao, Plymouth, MN (US); Micah A. Litow, Minneapolis, MN (US); Rajesh Iyer, Eden Prairie, MN (US); Dawit Y. Belete, Woodbury, MN (US); Simon E. Goldman, St. Louis Park, MN (US); Shawn D. Knowles, St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/360,882

(22) Filed: Jan. 28, 2009

(65) Prior Publication Data

US 2009/0128987 A1    May 21, 2009

Related U.S. Application Data

(63) Continuation of application No. 11/675,880, filed on Feb. 16, 2007, now Pat. No. 7,502,217.

(51) Int. Cl.
*H01G 4/236* (2006.01)
*H01G 4/228* (2006.01)
*A61N 1/00* (2006.01)

(52) U.S. Cl. ............ 361/307; 361/306.1; 607/2

(58) Field of Classification Search ......... 361/307, 361/302, 206.1; 607/2, 7
See application file for complete search history.

(56) References Cited

U.S. PATENT DOCUMENTS

| | | | |
|---|---|---|---|
| 4,441,780 A * | 4/1984 | Walters | 439/607.17 |
| 4,934,366 A | 6/1990 | Truex | |
| 4,966,564 A | 10/1990 | Foote | |
| 5,012,807 A | 5/1991 | Strutz | |
| 5,662,692 A * | 9/1997 | Paspa et al. | 607/37 |
| 5,825,608 A | 10/1998 | Duva | |
| 5,905,627 A | 5/1999 | Brendel | |
| 6,275,369 B1 | 8/2001 | Stevenson | |
| 6,765,780 B2 | 7/2004 | Brendel | |
| 6,767,779 B2 | 7/2004 | Parker et al. | |
| 6,835,084 B2 | 12/2004 | Poon | |
| 6,862,478 B1 * | 3/2005 | Goldstein | 607/37 |
| 6,882,248 B2 | 4/2005 | Stevenson | |
| 6,888,715 B2 | 5/2005 | Stevenson | |
| 6,985,347 B2 | 1/2006 | Stevenson | |
| 6,987,660 B2 | 1/2006 | Stevenson | |
| 6,999,818 B2 | 2/2006 | Stevenson | |
| 7,012,192 B2 | 3/2006 | Stevenson | |

(Continued)

OTHER PUBLICATIONS

U.S. Application No. 11/688,985 filed Mar. 21, 2007, Iyer.

(Continued)

*Primary Examiner*—Eric Thomas
*Assistant Examiner*—David M Sinclair
(74) *Attorney, Agent, or Firm*—Campbell Nelson Whipps LLC

(57) ABSTRACT

A filtering capacitor feedthrough assembly for an implantable active medical device is disclosed. The filtering capacitor feedthrough assembly includes a capacitor having an aperture, the capacitor is electrically grounded to an electrically conductive feedthrough ferrule or housing of the implantable active medical device. A terminal pin extends into the aperture and an electrically conductive continuous coil is disposed within the aperture and between the terminal pin and the capacitor. The electrically conductive continuous coil mechanically secures and electrically couples the terminal pin to the capacitor.

14 Claims, 5 Drawing Sheets

U.S. PATENT DOCUMENTS

| | | |
|---|---|---|
| 7,035,076 B1 | 4/2006 | Stevenson |
| 7,038,900 B2 | 5/2006 | Stevenson |
| 7,110,827 B2 | 9/2006 | Sage |
| 7,199,995 B2 | 4/2007 | Stevenson |
| 7,274,964 B2 | 9/2007 | Balsells |
| 7,502,217 B2 | 3/2009 | Zhao |
| 2001/0050837 A1 | 12/2001 | Stevenson |
| 2002/0166618 A1 | 11/2002 | Wolf |
| 2003/0163171 A1 | 8/2003 | Kast |
| 2004/0034393 A1 | 2/2004 | Hansen |
| 2004/0093038 A1 | 5/2004 | Biggs |
| 2004/0167582 A1 | 8/2004 | Tvaska |
| 2005/0060003 A1 | 3/2005 | Taylor |
| 2005/0095352 A1 | 5/2005 | Marshall |
| 2005/0197677 A1 | 9/2005 | Stevenson |
| 2005/0201039 A1 | 9/2005 | Stevenson |
| 2005/0248907 A1 | 11/2005 | Stevenson |
| 2006/0085043 A1 | 4/2006 | Stevenson |
| 2006/0167522 A1 | 7/2006 | Malinowski |
| 2006/0221543 A1 | 10/2006 | Stevenson |
| 2006/0259093 A1 | 11/2006 | Stevenson |
| 2007/0019362 A1 | 1/2007 | Stevenson |

OTHER PUBLICATIONS

PCT International Search Report dated Nov. 6, 2007.

* cited by examiner

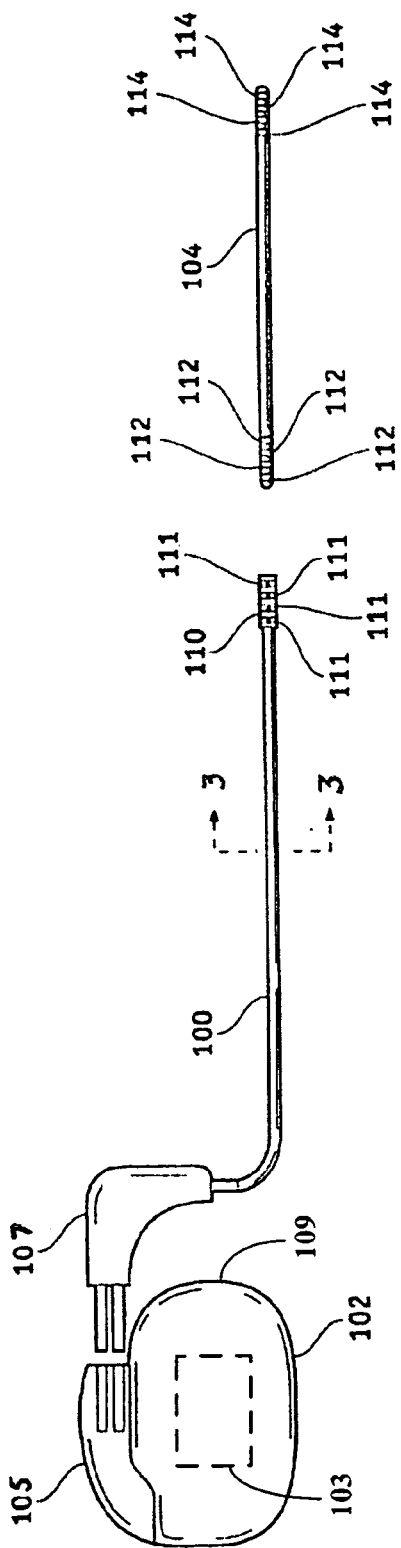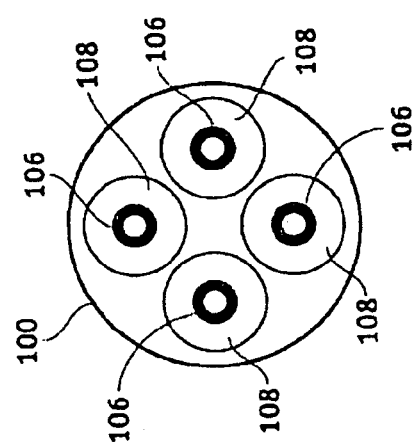
FIG. 2
FIG. 3

FILTERING CAPACITOR FEEDTHROUGH ASSEMBLY

CROSS-REFERENCE TO RELATED APPLICATIONS

This application is a continuation of application Ser. No. 11/675,880 filed Feb. 16, 2007, the contents of which is hereby incorporated by reference in its entirety.

FIELD

The present disclosure relates to a filtering capacitor feedthrough assembly for an implantable device.

BACKGROUND

Implantable active medical devices, such as cardiac disease rhythm management devices (pacemakers and defibrillators) and a variety of implantable muscle/nerve stimulators generally include a battery and battery-powered electronic pulse generator and may include a variety of sending, processing, and telemetry circuits all contained within a hermetically sealed housing or case and attached to a lead connector housing or block. The lead connector block is often affixed to the hermetically sealed housing with brackets, metal solder, and/or a medical grade adhesive.

Electronics within the hermetically sealed housing are conductively coupled to the lead connector block with an electrical feedthrough assembly. Electrical feedthroughs serve the purpose of providing a conductive path extending between the interior of a hermetically sealed container and a point outside the hermetically sealed housing. The conductive path through the feedthrough usually includes a conductor pin or terminal that is electrically insulated from the hermetically sealed housing. Feedthrough assemblies are known in the art to provide the conductive path and seal the electrical container from its ambient environment. Such feedthroughs include a ferrule, and an insulative material such as a hermetic glass or ceramic seal that positions and insulates the pin within the ferrule. Sometimes it is desired that the electrical device include a capacitor/filter within the ferrule and around the terminal, thus shunting any electromagnetic interference (EMI) and other high frequencies radiation at the entrance to the electrical device to which the feedthrough device is attached thereby preventing or substantially reducing EMI from entering the device. The capacitor electrically contacts the pin lead and the ferrule.

The pin lead/capacitor and capacitor/ferrule connection has been made using solder, weld, braze, and conductive adhesives. While this arrangement has proven to be highly reliable, it involves a variety of expensive manufacturing processes and parts that necessarily increase the cost of the resulting product.

BRIEF SUMMARY

The present disclosure relates to a filtering capacitor feedthrough assembly for an active implantable device. A continuous coil mechanically secures and electrically couples a terminal pin to filtering capacitor and/or a continuous coil mechanically secures and electrically couples a filtering capacitor to a ferrule or housing.

In a first embodiment, a filtering capacitor feedthrough assembly for an implantable active medical device is disclosed. The filtering capacitor feedthrough assembly includes a capacitor having an aperture, the capacitor is electrically grounded to an electrically conductive feedthrough ferrule or housing of the implantable active medical device. A terminal pin extends into the aperture and an electrically conductive continuous coil is disposed within the aperture and between the terminal pin and the capacitor. The electrically conductive continuous coil mechanically secures and electrically couples the terminal pin to the capacitor.

In another embodiment, an implantable active medical device includes a hermetically sealed housing, electronics disposed within the sealed housing, a lead connector attached to the hermetically sealed housing, and a filtering capacitor feedthrough assembly electrically connecting the electronics and the lead connector. The filtering capacitor feedthrough assembly includes a capacitor having an aperture and a terminal pin. The capacitor is electrically grounded to the hermetically sealed housing. The terminal pin extends into the aperture and the terminal pin electrically connects the electronics and the lead connector. An electrically conductive continuous coil is disposed within the aperture and between the terminal pin and the capacitor. The electrically conductive continuous coil mechanically securing and electrically coupling the terminal pin to the capacitor.

In a further embodiment, a filtering capacitor feedthrough assembly for an implantable active medical device includes a capacitor having an aperture, where the capacitor is electrically grounded to an electrically conductive feedthrough ferrule or housing of the implantable active medical device with an electrically conductive continuous coil. A terminal pin extends into the aperture, and the terminal pin is mechanically secured and electrically coupled to the capacitor.

BRIEF DESCRIPTION OF THE DRAWINGS

The invention may be more completely understood in consideration of the following detailed description of various embodiments of the invention in connection with the accompanying drawings, in which:

FIG. 2 is a schematic exploded view of an implantable active medical device;

FIG. 3 is a schematic cross-sectional view of a lead body shown in FIG. 2 taken along line 3-3;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
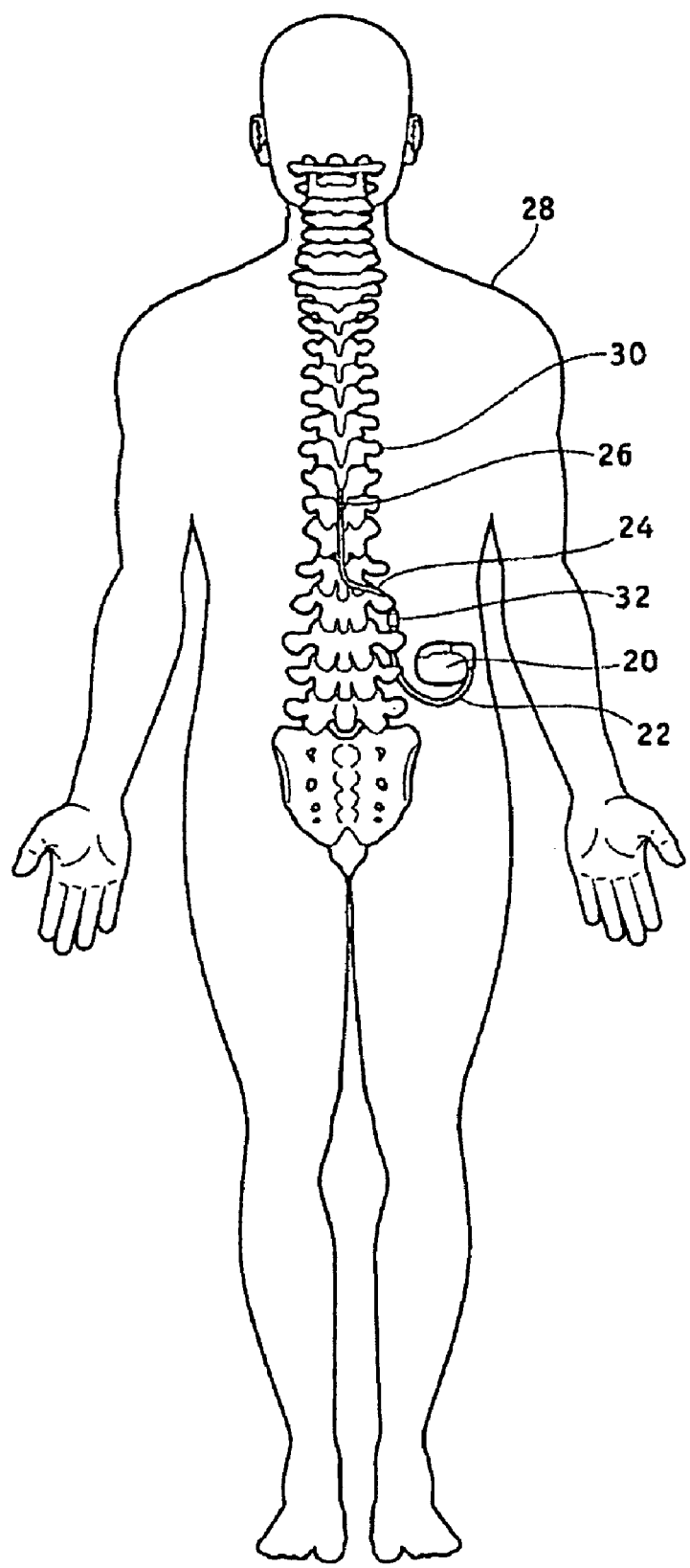
FIG. 1 is a schematic diagram of an active medical device implanted within a human body.

In the following description, reference is made to the accompanying drawings that form a part hereof, and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "active implantable medical device" includes, for example, a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, or a gastric pacemaker, and the like.

The terms "hermetic seal" and "hermetically sealed" are used interchangeably and refer to an airtight seal. This term is often used to describe electronic parts that are designed and intended to secure against the entry of microorganisms, water, oxygen, and the like, and to maintain the safety and quality of their contents.

The present disclosure relates to a filtering capacitor feedthrough assembly for an implantable device. In particular, this disclosure is directed to the use of a continuous coil to mechanically connect a feedthrough pin or terminal to a filtering capacitor and enable an electrical pathway between the capacitor and the feedthrough pin or terminal. This disclosure is also directed to the use of a continuous coil to mechanically connect a filtering capacitor to a ferrule or device housing and enable an electrical ground pathway between the capacitor and the ferrule or device housing. While the present invention is not so limited, an appreciation of various aspects of the invention will be gained through a discussion of the examples provided below.

FIG. 1 is a schematic diagram of an active medical device 20 implanted within a human body or patient 28. The implanted active medical device 20 is illustrated as a neurostimulator, however, the implanted active medical device 20 can be any "active implantable medical device" as described above and can be placed in any suitable location within a body cavity.

The illustrated active medical device 20 includes a lead extension 22 having a proximal end coupled to the active medical device 20, and a lead 24 having a proximal end coupled to a distal end 32 of the lead extension 22 and a distal end of the lead 24 coupled to one or more electrodes 26. In other embodiments, the lead 24 proximal end is coupled to the active medical device 20, without a need for a lead extension 22. The active medical device 20 can be implanted in any useful region of the body such as in the abdomen of a patient 28, and the lead 24 is shown placed somewhere along the spinal cord 30. In many embodiments, the active medical device 20 has one or two leads each having four to eight electrodes, as desired. Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous or discontinuous electrical stimulation, as desired.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously (e.g. the Model 3487A PISCES-QUAD® type lead available from Medtronic, Inc.), and some are designed to be surgically implanted (e.g. Model 3998 SPECIFY® type lead, also available form Medtronic, Inc.). In some embodiments, the lead 24 may contain a paddle at its distant end for housing electrodes 26. In many embodiments, electrodes 26 may include one or more ring contacts at the distal end of lead 24.

FIG. 2 is a schematic exploded view of the implantable active medical device described above and FIG. 3 is a schematic cross-sectional view of the lead extension 100 shown in FIG. 2 taken along line 3-3. The illustrated implantable active medical device includes a lead extension 100 configured to be coupled between an implantable active medical device 102 and the lead 104. The proximal portion of lead extension 100 includes a lead connector 107 configured to be received or plugged into housing lead connector 105 of an implantable active medical device 102 through a hermetically sealed housing 109 of the implantable active medical device 102 via a feedthrough assembly described below. The distal end of the lead extension 100 includes a connector 110 including internal contacts 111 and is configured to receive a proximal end of lead 104 having contacts 112 thereon. The distal end of the lead 104 includes distal electrodes 114 that are in electrical connection with corresponding contacts 112.

One illustrative lead extension 100 has a diameter of approximately 0.1 inch, which can be larger than that of lead 104 so as to make extension 100 more durable than lead 104. The lead extension 100 can differ from lead 104 in that each filer 106 in the lead body is helically wound or coiled in its own lumen 108 and not co-radially wound with the rest of the filers as can be the case in lead 104. The diameter of the lead can be approximately 0.05 inch. This diameter can be based upon the diameter of the needle utilized in the surgical procedure to deploy the lead and upon other clinical anatomical requirements. The length of such lead can be based upon other clinical anatomical requirements and can be 28 centimeters; however, other lengths are utilized to meet particular needs of specific patients and to accommodate special implant locations.

The active medical device 102 includes a hermetically sealed housing 109 defining a sealed housing interior. A battery and electronics are in electrical communication and are disposed within the sealed housing 109 interior. Battery and electronics 103 are illustrated schematically in FIG. 2 as a 'black box' within housing 109 interior. The electronics within the hermetically sealed housing 109 are conductively coupled to the lead connector block 105 with an electrical feedthrough assembly (described below). Electrical feedthroughs serve the purpose of providing a conductive path extending between the interior of a hermetically sealed housing 109 and the lead connector block 105 attached to the housing 109. The conductive path through the feedthrough assembly includes a conductor pin or terminal pin that is electrically insulated from the hermetically sealed housing 109. The feedthrough also include a ferrule, and an electrically insulating material such as a hermetic glass or ceramic seal that positions and insulates the pin within the ferrule. Filtered feedthroughs include a capacitor within the ferrule and around the terminal pin to shunt any electromagnetic interference (EMI) at high frequencies at the entrance to the electrical device to which the feedthrough device is attached. The capacitor electrically contacts the terminal pin (with active plates) and the ferrule (with ground plates). The terminal pin electrically connects the electronics within the sealed housing to the lead connector.

Figure 4:
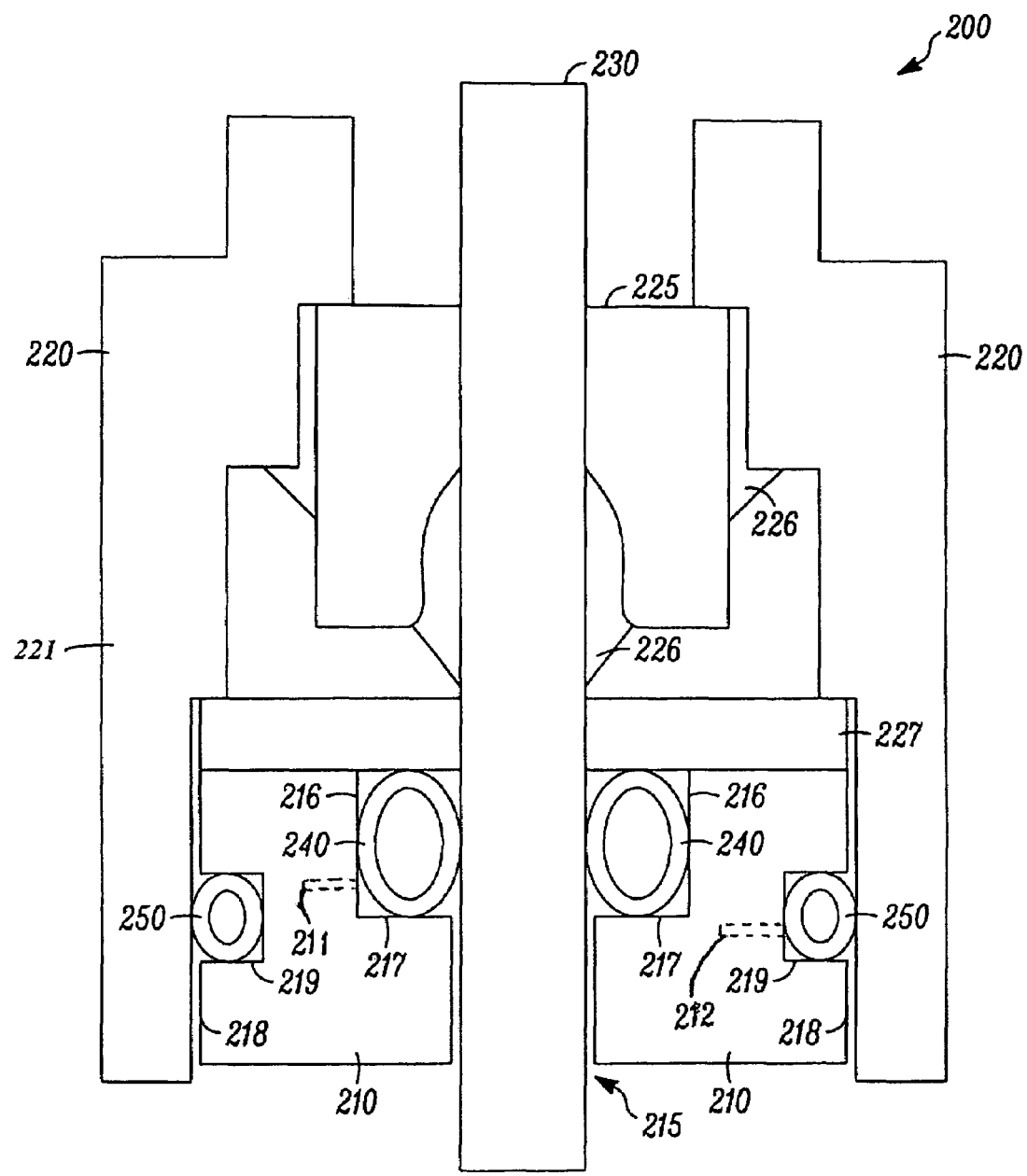
FIG. 4 is a schematic cross-sectional diagram of an illustrative filtering capacitor feedthrough assembly.

FIG. 4 is a schematic cross-sectional diagram of an illustrative filtering capacitor feedthrough assembly 200. The filtering capacitor feedthrough assembly 200 includes a capacitor 210 having an aperture 215 defined by an inner surface 216 of the capacitor 210. In many embodiments, the aperture 215 extends all the way through the capacitor 210 forming a cylindrical lumen or cylindrical aperture through the capacitor 210. In some embodiments, the aperture 215 defines a ledge 217 within the aperture 215 creating a cylindrical lumen having a first lumen diameter and a second lumen diameter, where the first lumen diameter is less than the second lumen diameter. The inner surface 216 of the capacitor 210 is in electrical contact with active plates 211 within the capacitor 210. An outer surface 218 of the capacitor 210 is in electrical contact with ground plates 212 within the capacitor 210. A single active plate 211 and a single ground plate 212 is illustrated, however it is understood that the capacitor 210 includes a plurality of active plates 211 and ground plates 212 as is known in the art.

A terminal pin 230 extends into the aperture 215 of the capacitor 210. In many embodiments, the terminal pin 230 extends through the aperture 215 of the capacitor 210. An electrically conductive continuous coil 240 is disposed within the aperture 215 and between and in contact with both the terminal pin 230 and the capacitor 210. The electrically conductive continuous coil 240 mechanically secures and electrically couples the terminal pin 230 to the capacitor 210 inner surface 216. In many embodiments, the electrically conductive continuous coil 240 has an inner diameter $R_D$ (see FIGS. 5A and 5B) slightly less than an outer diameter of the terminal pin 230 and the terminal pin 230 is disposed within the inner diameter $R_D$ of the continuous coil 240. Thus, the continuous coil 240 is axially or radially disposed about the terminal pin 230.

In embodiments where a ledge 217 is within the aperture 215, the conductive continuous coil 240 is disposed on or adjacent to the ledge 217. In some embodiments, the conductive continuous coil 240 is fixed to the terminal pin 230 and/or the inner surface 216 of the capacitor 210. The conductive continuous coil 240 can be fixed with any useful method or material such as, for example, solder, weld, braze, and/or conductive adhesive.

The terminal pin 230 extends through the ferrule 220 or housing 221 and the terminal pin 230 is in a non-conductive relation to the ferrule 220 or housing 221. An insulator 225 is disposed between the terminal pin 230 and the ferrule 220 or housing 221. The insulator 225 is disposed fixed to the terminal pin 230 and the ferrule 220 or housing 221 with solder, weld, braze, and/or adhesive 226, as desired to provide a hermetic seal. An optional second insulator 227 is disposed within the ferrule 220 or housing 221 and adjacent to the capacitor 210.

The outer surface 218 of the capacitor 210 is electrically grounded to an electrically conductive feedthrough ferrule 220 or housing 221 of the implantable active medical device. In some embodiments, an electrically conductive continuous coil 250 is disposed between the outer surface 218 of the capacitor 210 and the electrically conductive feedthrough ferrule 220 or housing 221. The electrically conductive continuous coil 250 mechanically secures and electrically couples the capacitor 210 to the electrically conductive feedthrough ferrule 220 or housing 221. In many embodiments, the electrically conductive continuous coil 250 has an outer diameter slightly greater than an inner diameter or circumference of the electrically conductive feedthrough ferrule 220 or housing 221. Thus, the continuous coil 250 is axially or radially disposed about the capacitor 210. In some embodiments, a ledge 219 is defined by the outer surface 218 of the capacitor 210 and the conductive continuous coil 250 is disposed on or adjacent to the ledge 219.

While only one continuous coil 240 or 250 is shown mechanically securing and electrically coupling adjacent surfaces, two or more continuous coils 240 or 250 can mechanically secure and electrically couple adjacent surfaces, as desired. In addition, solder, weld, braze or conductive adhesive can be placed adjacent to continuous coil 240 or 250 to assist in mechanically securing and electrically coupling adjacent surfaces, as desired.

Figures 5A, 5B:
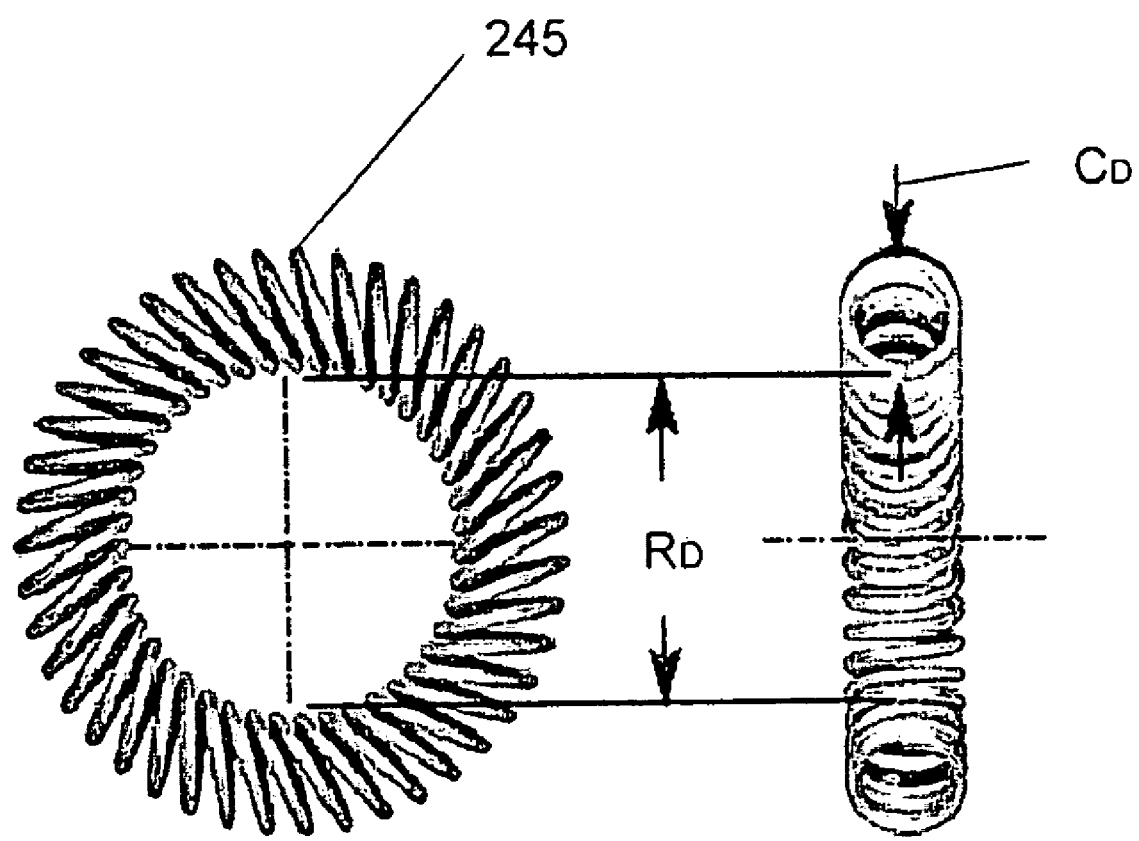
FIG. 5A is a top view of an illustrative continuous coil utilized in a filtering capacitor feedthrough assembly.
FIG. 5B is a cross-sectional side view of the continuous coil and shown in FIG. 5A.

FIG. 5A is a top view of an illustrative continuous coil utilized in the filtering capacitor feedthrough assembly described herein. FIG. 5B is a cross-sectional view of the continuous coil shown in FIG. 5A. In many embodiments, the continuous coil is formed of a conductive wire 245 helically wound to form an annular ring referred to herein as a continuous coil. The continuous coil has an inner diameter $R_D$ and a coil diameter $C_D$. In many embodiments, the terminal pin (described above) is disposed within the inner diameter of the continuous coil (e.g., coil 240 of FIG. 4) and compresses the continuous coil diameter $C_D$ against the inner surface of the capacitor aperture (described above) to form the mechanical interference fit and conductive contact between the terminal pin and the capacitor. In many embodiments, the capacitor outer surface (described above) is disposed within the inner diameter of the continuous coil (e.g., coil 250 of FIG. 4) and compresses the continuous coil diameter $C_D$ against the inner surface of the housing or ferrule (described above) to form the mechanical interference fit and conductive (ground) contact between the capacitor and the housing or ferrule.

The inner diameter $R_D$ and the 2×(coil diameter $C_D$) equals an outer diameter of the continuous coil. The continuous coil is shown in an uncompressed state where the coil diameter $C_D$ has a substantially circular form, in a compressed state (axial compression as shown by the arrows $C_D$) the coil diameter $C_D$ distends or elastically deforms to an oval form (see FIG. 4). Compressing the continuous coil between adjacent surfaces mechanically secures and electrically couples adjacent surfaces via an interference elastic axial compression fit of the continuous coil diameter $C_D$. As the continuous coil is compressed between adjacent surfaces, the coil will also cant or deflect up to 40%. In many embodiments, the working deflection of the continuous coil is from 10 to 35%.

The continuous coil can have any useful dimensions. In many terminal pin to capacitor embodiments, the continuous coil has an inner diameter $R_D$ in a range from 150 to 800 micrometers, or 250 to 750 micrometers, or 350 to 550 micrometers and a coil diameter $C_D$ in a range from 250 to 500 micrometers, or 325 to 425 micrometers and an outer diameter in a range from 750 to 1750 micrometers, or from 1000 to 1400 micrometers and a wire diameter in a range from 25 to 100 micrometers. In many capacitor to ferrule embodiments, the continuous coil has an inner diameter $R_D$ suitable to extend around the capacitor in a range from 500 to 5000 micrometers and a wire diameter in a range from 100 to 1000 micrometers. The continuous coil can be formed of any useful conductive material such as metals, for example, gold, silver, titanium, stainless steel, platinum, copper, and alloys or mixtures thereof.

Figure 6:
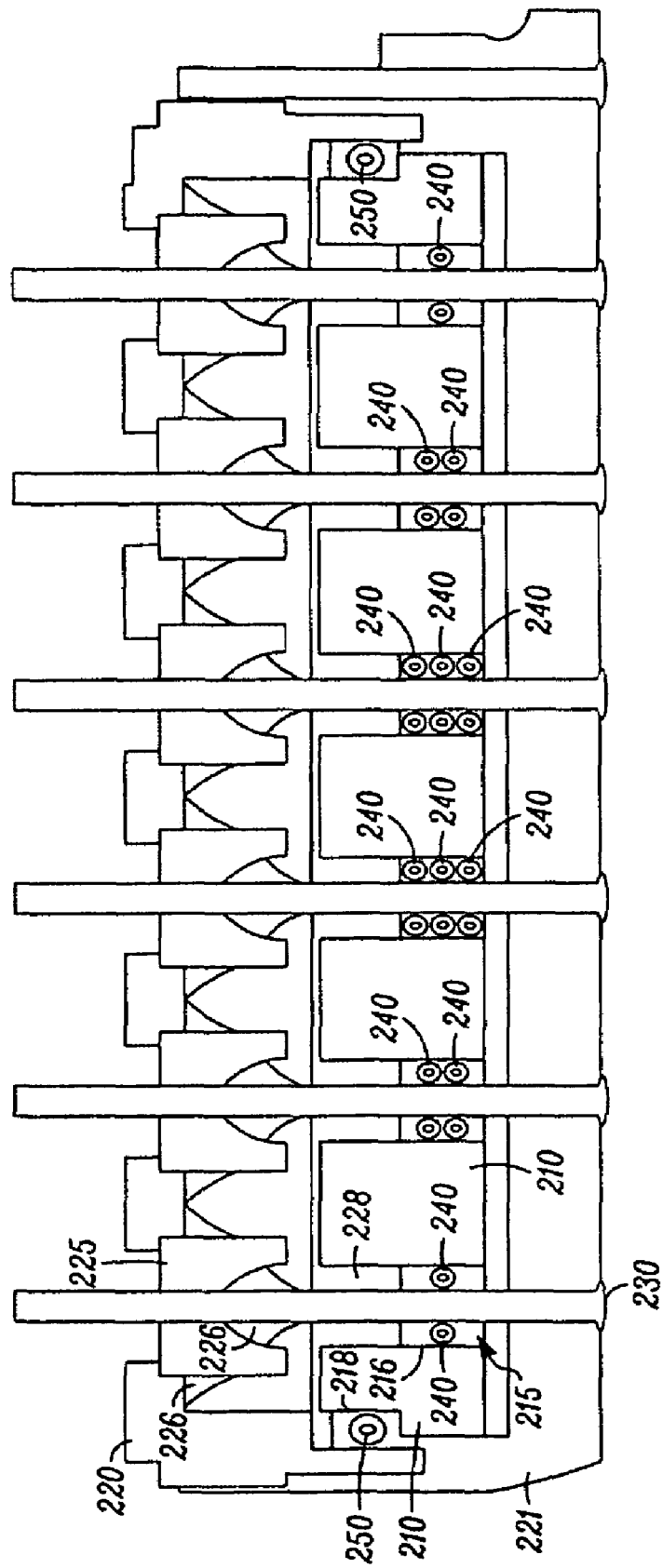
FIG. 6 is a schematic cross-sectional diagram of an illustrative multi-pin filtering capacitor feedthrough assembly.

FIG. 6 is a schematic cross-sectional diagram of an illustrative multi-pin or multipolar filtering capacitor feedthrough assembly 201. In this embodiment, six terminal pins 230 are disposed through the feedthrough assembly 201. The first terminal pin 230 is now described. The five remaining pins 230 have a substantially similar description and is not repeated but understood to be the same as the first terminal pin 230 assembly.

The filtering capacitor feedthrough assembly 201 includes a capacitor 210 having a plurality of apertures 215 defined by an inner surface 216 of the capacitor 210. In many embodiments, the apertures 215 extend all the way through the capacitor 210 forming a plurality of cylindrical lumens through the capacitor 210. The inner surface 216 of the capacitor 210 is in electrical contact with active plates within the capacitor 210. An outer surface 218 of the capacitor 210 is in electrical contact with ground plates within the capacitor 210.

A terminal pin 230 extends into each corresponding aperture 215 of the capacitor 210. In many embodiments, the terminal pin 230 extends through the aperture 215 of the capacitor 210. One or more electrically conductive continuous coils 240 are disposed within the aperture 215 and between the terminal pin 230 and the capacitor 210. The electrically conductive continuous coils 240 mechanically secure and electrically couple the terminal pins 230 to the capacitor 210 inner surface 216. In many embodiments, the electrically conductive continuous coils 240 have an inner diameter (see FIGS. 5A and 5B) slightly less than an outer diameter of the terminal pins 230. Thus, the continuous coil 240 is axially disposed about the terminal pin 230. In some embodiments, the conductive continuous coils 240 are fixed to the corresponding terminal pin 230 or inner surface 216 of the capacitor 210. The conductive continuous coils 240 can be fixed with any useful method or material such as, for example, solder, weld, braze or conductive adhesive.

The terminal pin 230 extends through the ferrule 220 and housing 221 and is in a non-conductive relation to the ferrule 220 and housing 221. An insulator 225 is disposed between the terminal pin 230 and the ferrule 220. The insulator 225 is disposed fixed to the terminal pin 230 and the ferrule 220 with solder, weld, braze or adhesive 226, as desired to provide a hermetic seal.

The outer surface 218 of the capacitor 210 is electrically grounded to an electrically conductive feedthrough ferrule 220 of the implantable active medical device. In some embodiments, an electrically conductive continuous coil 250 is disposed between the outer surface 218 of the capacitor 210 and the electrically conductive feedthrough ferrule 220. The electrically conductive continuous coil 250 mechanically secures and electrically couples the capacitor 210 to the electrically conductive feedthrough ferrule 220. In many embodiments, the electrically conductive continuous coil 250 has an outer diameter slightly greater than an inner diameter of the electrically conductive feedthrough ferrule 220. Thus, the continuous coil 250 is axially disposed about the capacitor 210.

In this embodiment, one, two and three continuous coils 240 are shown mechanically securing and electrically coupling adjacent surfaces, any number of continuous coils can mechanically secure and electrically couple adjacent surfaces, as desired. In addition, solder, weld, braze or conductive adhesive 228 can be placed adjacent to continuous coils 240 or 250 to assist in mechanically securing and electrically coupling adjacent surfaces, as desired.

Utilization of the continuous coils described herein, provides a robust mechanical interference compression attachment between surfaces within the filtering capacitor feedthrough assembly. The continuous coils can function as a strain relief structure during feedthrough pin deflection. In addition the continuous coils described herein provide a multitude of electrical connections between the terminal pin and the capacitor and/or the capacitor and the housing or ferrule.

Thus, embodiments of the FILTERING CAPACITOR FEEDTHROUGH ASSEMBLY are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A filtering capacitor feedthrough assembly for an implantable active medical device comprising:
   a capacitor having an aperture, the capacitor electrically grounded to an electrically conductive feedthrough ferrule or housing of the implantable active medical device;
   a terminal pin extending into the aperture; and
   an electrically conductive continuous coil disposed within the aperture between the terminal pin and the capacitor, the continuous coil being fixed to the terminal pin and the capacitor with solder, weld, braze or conductive adhesive, the continuous coil comprising an inner diameter defined by a plurality of coils, each coil having a coil diameter different than the inner diameter, with the terminal pin extending through the inner diameter of the continuous coil so that the plurality of coils circumferentially surround the terminal pin, the electrically conductive continuous coil mechanically securing and electrically coupling the terminal pin to the capacitor.

2. A filtering capacitor feedthrough assembly according to claim 1, wherein the continuous coil is compressed between the terminal pin and the capacitor.

3. A filtering capacitor feedthrough assembly according to claim 1, wherein the plurality of coils are canted.

4. A filtering capacitor feedthrough assembly according to claim 1, comprising two or more continuous coils disposed within the aperture and between the terminal pin and the capacitor, and mechanically securing and electrically coupling the terminal pin to the capacitor.

5. A filtering capacitor feedthrough assembly according to claim 1, further comprising a conductive adhesive, solder, or braze disposed within the aperture.

6. A filtering capacitor feedthrough assembly according to claim 1, wherein the aperture defines a ledge and the continuous coil is disposed on the ledge.

7. A filtering capacitor feedthrough assembly according to claim 1, further comprising a second electrically conductive continuous coil disposed between the capacitor and the electrically conductive feedthrough ferrule or housing of the implantable active medical device, the second electrically conductive continuous coil mechanically securing and electrically coupling the capacitor and the electrically conductive feedthrough ferrule or housing of the implantable active medical device.

8. An implantable active medical device comprising:

a hermetically sealed housing;

electronics disposed within the sealed housing;

a lead connector attached to the hermetically sealed housing; and a filtering capacitor feedthrough assembly electrically connecting the electronics and the lead connector, the filtering capacitor feedthrough assembly comprising:

a capacitor having an aperture, the capacitor electrically grounded to the hermetically sealed housing;

a terminal pin extending into the aperture, the terminal pin electrically connecting the electronics and the lead connector; and an electrically conductive continuous coil disposed within the aperture between the terminal pin and the capacitor, the continuous coil being fixed to the terminal pin and the capacitor with solder, weld, braze or conductive adhesive, the continuous coil comprising an inner diameter defined by a plurality of coils, each coil having a coil diameter different than the inner diameter, with the terminal pin extending through the inner diameter of the continuous coil so that the plurality of coils circumferentially surround the terminal pin, the electrically conductive continuous coil mechanically securing and electrically coupling the terminal pin to the capacitor.

9. An implantable active medical device according to claim 8, wherein the continuous coil is compressed between the terminal pin and the capacitor.

10. An implantable active medical device according to claim 8, wherein the plurality of coils are canted.

11. An implantable active medical device according to claim 8, comprising two or more continuous coils disposed within the aperture and between the terminal pin and the capacitor, and mechanically securing and electrically coupling the terminal pin to the capacitor.

12. An implantable active medical device according to claim 8, further comprising a conductive adhesive, solder, or braze disposed within the aperture.

13. An implantable active medical device according to claim 8, wherein the aperture defines a ledge and the electrically conductive continuous coil is disposed on the ledge.

14. An implantable active medical device according to claim 8, further comprising a second electrically conductive continuous coil disposed between the capacitor and the hermetically sealed housing, the second electrically conductive continuous coil mechanically securing and electrically coupling the capacitor and the hermetically sealed housing.

* * * * *